(12) United States Patent
Jaax et al.

(10) Patent No.: US 7,610,100 B2
(45) Date of Patent: Oct. 27, 2009

(54) METHODS AND SYSTEMS FOR TREATING OSTEOARTHRITIS

(75) Inventors: Kristen N. Jaax, Saugus, CA (US); Rafael Carbunaru, Studio City, CA (US); Todd K. Whitehurst, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 301 days.

(21) Appl. No.: 11/322,763

(22) Filed: Dec. 30, 2005

(65) Prior Publication Data

US 2007/0156180 A1 Jul. 5, 2007

(51) Int. Cl.
A61M 37/00 (2006.01)
A61N 1/05 (2006.01)
A61N 1/36 (2006.01)
A61B 18/14 (2006.01)

(52) U.S. Cl. .............................. 607/62; 600/12; 600/13; 600/14; 606/32; 607/46; 607/48; 607/50; 607/51; 607/52; 607/59

(58) Field of Classification Search ....................... None
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |
| 4,562,751 A | 1/1986 | Nason et al. | |
| 4,612,934 A | 9/1986 | Borkan | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,501,703 A | 3/1996 | Holsheimer | |
| 5,728,396 A | 3/1998 | Peery et al. | |
| 5,938,688 A | 8/1999 | Schiff | |
| 5,941,906 A | 8/1999 | Barreras, Sr. et al. | |
| 6,016,449 A | 1/2000 | Fischell et al. | |
| 6,051,017 A | 4/2000 | Loeb et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,458,171 B1 | 10/2002 | Tsukamoto | |
| 6,487,446 B1 | 11/2002 | Hill et al. | |
| 6,516,227 B1 | 2/2003 | Meadows et al. | |
| 6,526,318 B1 * | 2/2003 | Ansarinia | 607/46 |
| 6,539,263 B1 | 3/2003 | Schiff et al. | |
| 6,553,263 B1 | 4/2003 | Meadows et al. | |

(Continued)

FOREIGN PATENT DOCUMENTS

WO WO 01/82398 A1 1/2001

(Continued)

OTHER PUBLICATIONS

U.S. Appl. No. 11/317,460, filed Dec. 2005, Jaax et al.*

(Continued)

Primary Examiner—Shaojia Anna Jiang
Assistant Examiner—Eric S Olson
(74) Attorney, Agent, or Firm—Darby & Darby PC

(57) ABSTRACT

Methods of treating osteoarthritis include applying at least one stimulus to a stimulation site within a patient with an implanted system control unit in accordance with one or more stimulation parameters. Systems for treating osteoarthritis include a system control unit configured to apply at least one stimulus to a stimulation site within a patient in accordance with one or more stimulation parameters.

20 Claims, 14 Drawing Sheets

U.S. PATENT DOCUMENTS

| | | |
|---|---|---|
| 6,610,713 B2 * | 8/2003 | Tracey .................. 514/343 |
| 6,620,151 B2 | 9/2003 | Blischak et al. |
| 6,666,845 B2 | 12/2003 | Hooper et al. |
| 6,735,474 B1 | 5/2004 | Loeb et al. |
| 6,740,072 B2 | 5/2004 | Starkweather et al. |
| 6,760,626 B1 | 7/2004 | Boveja |
| 6,770,067 B2 | 8/2004 | Lorenzen et al. |
| 7,429,471 B2 * | 9/2008 | Brighton ............ 435/173.8 |
| 2001/0046625 A1 | 11/2001 | Ruth, II et al. |
| 2001/0053476 A1 | 12/2001 | Ruth et al. |
| 2004/0054379 A1 * | 3/2004 | Carroll et al. ............. 607/2 |
| 2005/0143789 A1 * | 6/2005 | Whitehurst et al. ........ 607/46 |
| 2005/0228451 A1 * | 10/2005 | Jaax et al. ................ 607/2 |
| 2006/0161277 A1 * | 7/2006 | Robinson ................ 700/94 |
| 2006/0178709 A1 * | 8/2006 | Foster et al. ............. 607/45 |
| 2006/0200057 A1 * | 9/2006 | Sterling ................... 602/5 |
| 2007/0049988 A1 * | 3/2007 | Carbunaru et al. ......... 607/59 |

FOREIGN PATENT DOCUMENTS

| | | |
|---|---|---|
| WO | WO 03/005465 A1 | 1/2003 |

OTHER PUBLICATIONS

U.S. Appl. No. 11/317,465, filed Dec. 2005, Jaax et al.*
U.S. Appl. No. 11/317,466, filed Dec. 2005, Jaax et al.*
U.S. Appl. No. 11/430,541, filed May 2006, Jaax et al.*
U.S. Appl. No. 11/478,001, filed Jun. 2006, Tamarkin et al.*
U.S. Appl. No. 11/479,487, filed Jun. 2006, Foster et al.*
Pelletier et al., "Intraarticular Injections with Methylprednisone Acetate Reduce Osteoarthritic Lesions in Parallel With Chondrocyte Stromelysin Synthesis in Experimental Osteoarthritis" Arthritis and Rheumatism (1994) vol. 37, No. 3, pp. 414-423.*
The Merck Manual of Diagnosis and Therapy, Seventeenth Edition, published 1999 by Merck Research Laboratories, ed. by Beers and Berkow, pp. 449-451.*

* cited by examiner

METHODS AND SYSTEMS FOR TREATING OSTEOARTHRITIS

BACKGROUND

Osteoarthritis is a type of arthritis that is caused by the breakdown and eventual loss of cartilage in one or more joints. Cartilage is a protein substance that serves as a "cushion" between the bones of the joints. Osteoarthritis is also known as degenerative arthritis. Among the over 100 different types of arthritis conditions, osteoarthritis is the most common, affecting over twenty million people in the United States.

Osteoarthritis often affects synovial joints, such as the knees, hips, fingers, thumbs, neck, and spine. Synovial joints consist of two bone ends covered by articular cartilage. Osteoarthritis may be caused by meniscal or ligament injury, pyogenic infection, ligamentous instability, joint fracture, obesity, or natural degenerative causes.

Severe forms of the disease are extremely disabling and restrict a patient's lifestyle. Patients with osteoarthritis often suffer from depression, anxiety, feelings of helplessness, job limitations, and the inability to perform daily activities. The financial burden resulting from medical treatment and wages lost because of osteoarthritis is often great.

A number of techniques are currently used to treat osteoarthritis. Non-surgical techniques for treating osteoarthritis include weight loss, rest, physical therapy, orthotics, and heat. Weight loss alleviates stress on an affected joint and is sometimes effective in treating osteoarthritis. Short-term rest of an affected joint may be effective in temporarily relieving pain. However, longer periods of rest may result in muscle atrophy and decreased joint mobility. Physical therapy can improve the flexibility and strength of the muscles surrounding an arthritic joint, thus changing the distribution of the stress in the joint and slowing the progression of the disease. Orthotics such as insoles or heeled sport shoes can also improve the distribution of force across an affected joint. Heat applied to an affected joint is sometimes effective in treating osteoarthritis because it may produce analgesia and decrease muscle spasms. However, many of these non-surgical techniques are frequently unsuccessful in treating osteoarthritis. Where these non-surgical techniques are successful, they generally offer only short-term relief.

Pharmacologic therapy for osteoarthritis is primarily used to alleviate the pain associated with osteoarthritis rather than to treat the cause of the disease. Analgesic agents used to treat osteoarthritis include non-steroidal anti-inflammatory drugs such as COX-2 inhibitors (e.g., ViOXX™, Celebrex™). These drugs provide treatment of pain and inflammation in osteoarthritis, but may be of limited efficacy in more severe cases.

Intraarticular injection of corticosteroids or other suitable agents may also be used to treat osteoarthritis. Intraarticular injections may be appropriate when non-steroidal anti-inflammatory dugs (NSAIDs) are insufficient to control the pain symptoms of osteoarthritis. Intraarticular corticosteroids slow catabolism of cartilage and osteophyte formation and have been found to be effective for short-term pain relief.

Surgical interventions for osteoarthritis include arthroscopy, arthroplasty, and chondrocyte grafting. Arthroscopy involves the removal of damaged cartilage and has been widely used for knee osteoarthritis. Arthroscopy offers temporary improvement in some patients. However, some patients do not react well to arthroscopy and their symptoms of osteoarthritis may actually increase.

Chondrocyte grafting involves the implantation of cultivated chondrocytes into a joint to replace damaged cartilage. Chondrocyte grafting is a difficult and costly procedure and often does not successfully alleviate the symptoms of osteoarthritis.

In arthroplasty, a joint that is affected by osteoarthritis is entirely replaced with a prosthetic joint. Arthroplasty is typically targeted towards older patients with modest activity levels due to the limited lifespan of prosthetic joints. Prosthetic joints last approximately ten years and can be replaced a maximum of two times. Hence, arthroplasty is not a viable option for many younger patients with osteoarthritis.

The symptoms of osteoarthritis may also be controlled through the use of a transcutaneous electrical nerve stimulation (TENS) system which masks local pain sensations with a fine tingling sensation. However, TENS devices can produce significant discomfort and can only be used intermittently.

SUMMARY

Methods of treating osteoarthritis include applying at least one stimulus to a stimulation site within a patient with an implanted system control unit in accordance with one or more stimulation parameters.

Systems for treating osteoarthritis include a system control unit configured to apply at least one stimulus to a stimulation site within a patient in accordance with one or more stimulation parameters.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for treating osteoarthritis are described herein. An implanted system control unit (SCU) is configured to apply at least one stimulus to a stimulation site within a patient in accordance with one or more stimulation parameters. The stimulus is configured to treat osteoarthritis and may include electrical stimulation, drug stimulation, chemical stimulation, thermal stimulation, electromagnetic stimulation, optical stimulation, mechanical stimulation, and/or any other suitable stimulation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
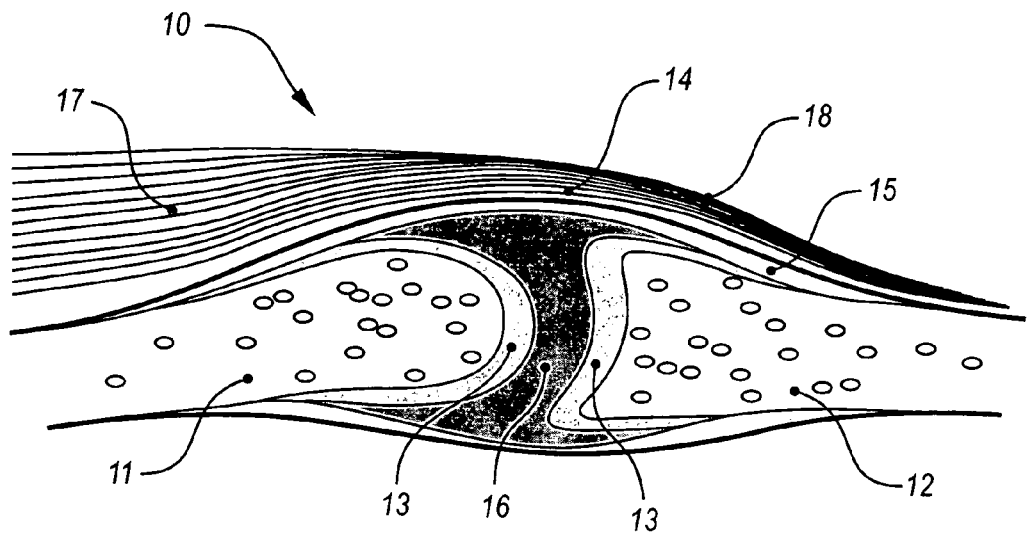
FIG. 1A illustrates an exemplary healthy joint within a patient.

FIG. 1A illustrates an exemplary healthy joint (10) within a patient. In a healthy joint (10), the ends of moveably jointed bones (11, 12) are encased in smooth cartilage (13). The cartilage (13) is a protein substance that serves as a "cushion" between the bones (11, 12) of the joint (10). The bones (11, 12) and the cartilage (13) are protected by a tough membrane called the joint capsule (14). The inner surface of the joint capsule (14) is lined with a synovial membrane (15) that produces a synovial fluid (16) that nourishes and lubricates the cartilage (13). Muscles (17), connective tendons (18), and other tissue (e.g., ligaments) surround the joint capsule (14). These tissues keep the bones (11, 12) stable and allow the joint (10) to bend and move.

Figure 1B:
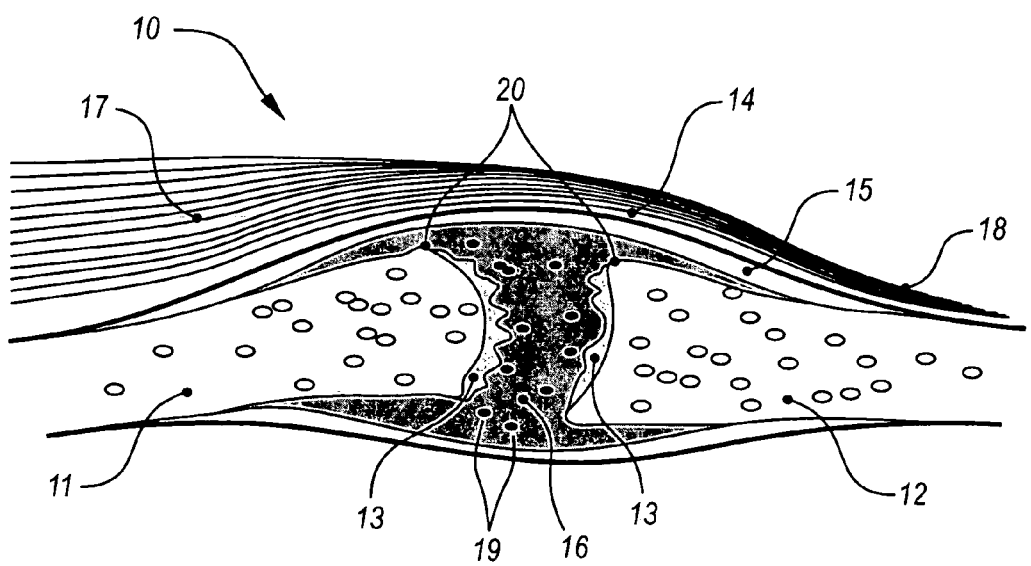
FIG. 1B illustrates the effect of osteoarthritis on the joint of FIG. 1A.

FIG. 1B illustrates the effect of osteoarthritis on the joint (10) of FIG. 1A. As shown in FIG. 1B, osteoarthritis causes the cartilage (13) to become worn away from the ends of the bones (11, 12). Fragments of cartilage (19) may break off from the bones (11, 12) and become suspended in the synovial fluid (16). Bone spurs (20) may grow out from the edge of the bones (11, 12). Osteoarthritis may also cause the synovial membrane (15) to produce an increased amount of synovial fluid (16). Altogether, the joint (10) may become swollen and/or feel stiff and sore.

Figure 2A:
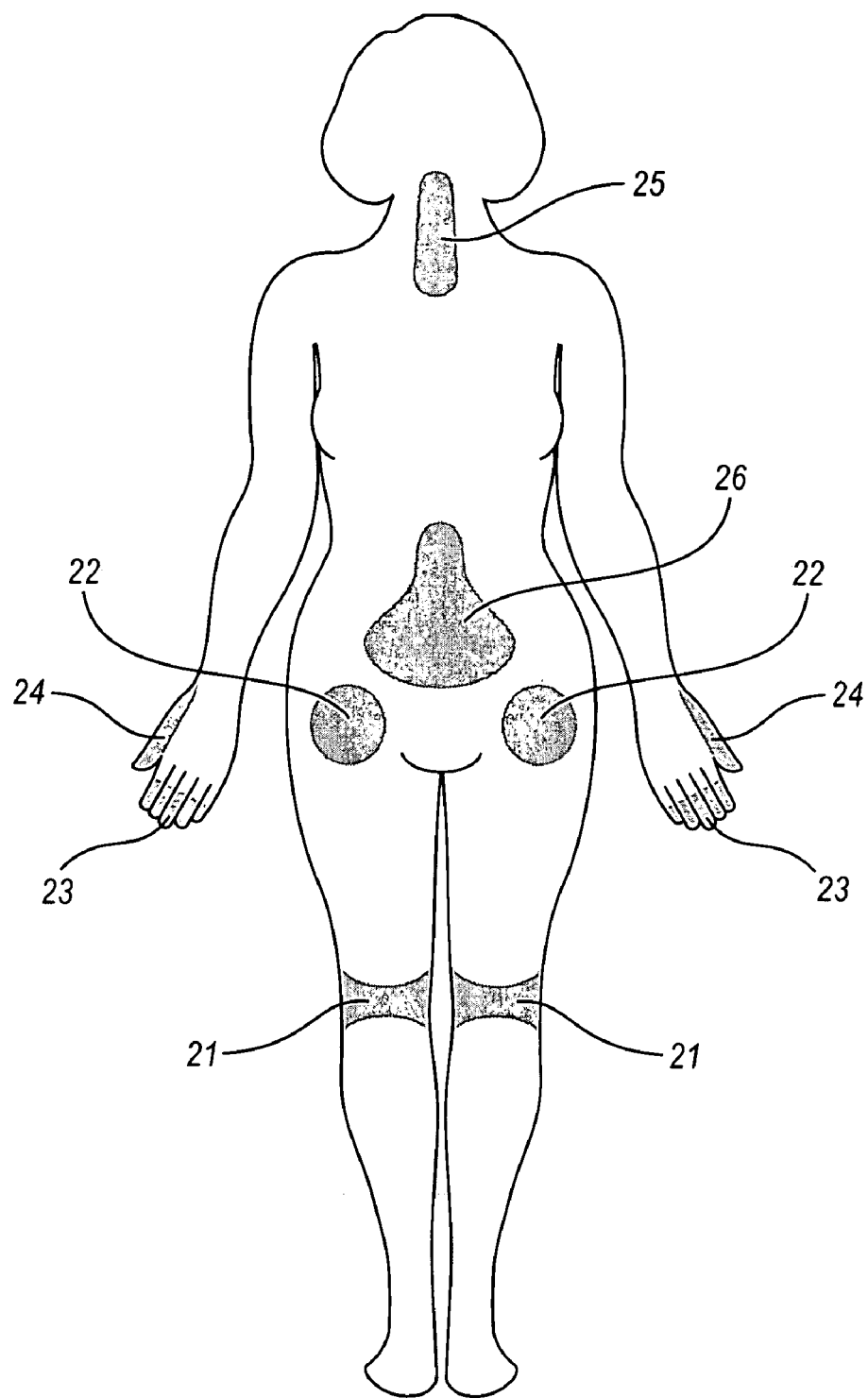
FIG. 2A illustrates a number of common locations within a patient that may be affected by osteoarthritis.

FIG. 2A illustrates a number of common locations within a patient that may be affected by osteoarthritis. It will be recognized that the locations illustrated in FIG. 2A are merely exemplary of the many different locations within a patient that may be affected by osteoarthritis. For example, osteoarthritis may affect a patient's knees (21), hips (22), fingers (23), thumbs (24), neck (25), and spine (26).

Osteoarthritis in the hips (22) can cause pain, stiffness, and severe disability. Patients may feel the pain in their hips (22), groin, inner thigh, buttocks, or knees.

Osteoarthritis in the fingers (23) may cause the fingers (23) to become enlarged and gnarled. The disease may cause small, bony knobs to appear on the end joints of the fingers (23). These knobs are referred to as Heberden's nodes. Similar knobs, called Bouchard's nodes, can appear on the middle joints of the fingers (23). Affected fingers (23) may ache or be stiff and numb. More women than men suffer from osteoarthritis in the fingers (23), and they develop it especially after menopause. The base of the thumb joint (24) may also be similarly affected by osteoarthritis.

Osteoarthritis in the neck (25) and spine (26) may cause stiffness and pain in the neck or in the lower back. It may also cause weakness or numbness of the arms or legs. Osteoarthritis in the neck (25) and spine (26) is often debilitating and may result in the patient being bed-ridden.

Figure 2B:
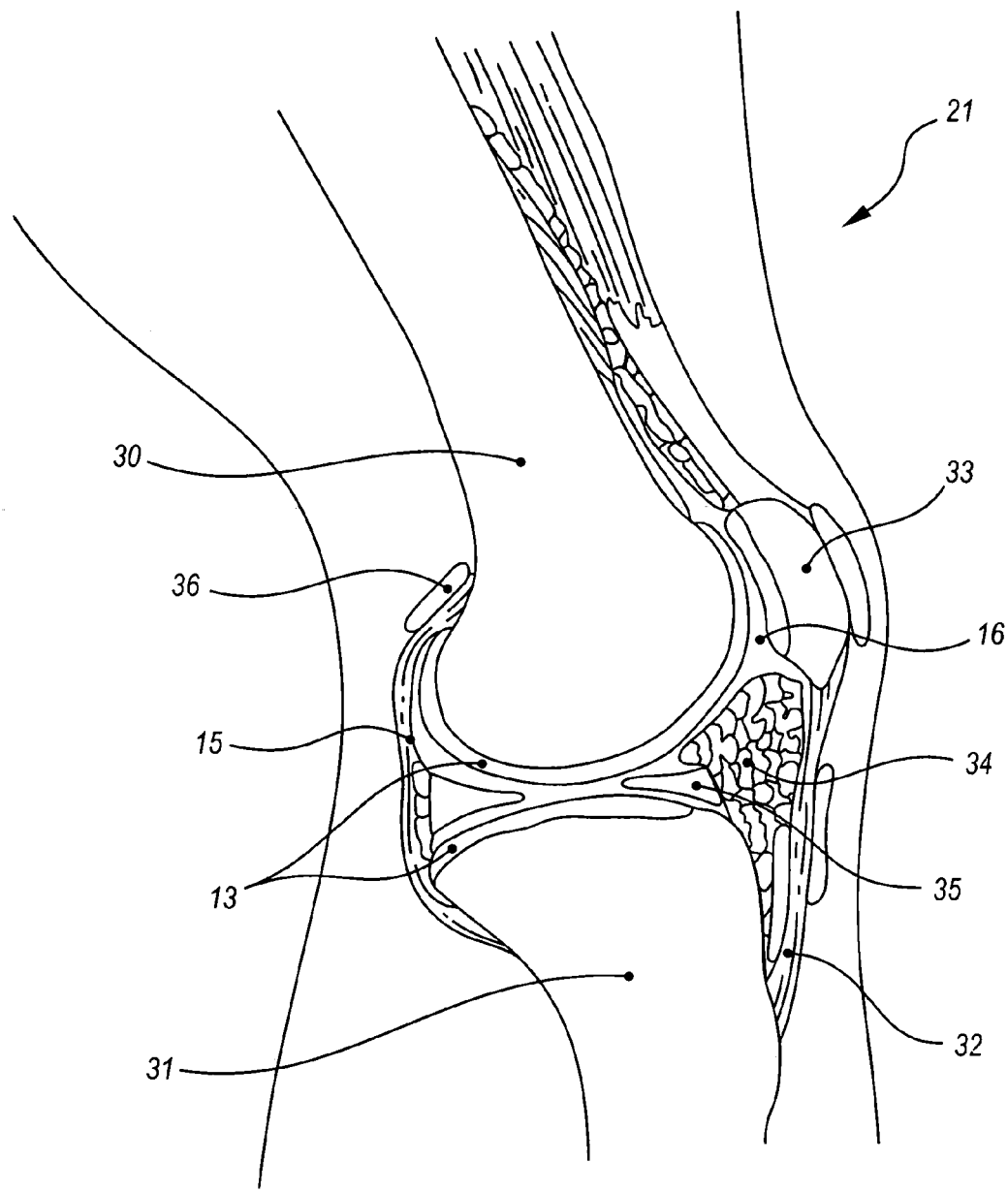
FIG. 2B is a diagram of the knee joint.

One of the most common locations for osteoarthritis is in the knees (21). FIG. 2B is a diagram of the knee joint (21). As shown in FIG. 2B, the knee joint (21) permits movement between the femur (30) and tibia (31). The patella (33), also known as the knee cap, rides on the knee joint (21) as the knee bends. The meniscus (35) is a C-shaped piece of tissue which fits into the joint between the tibia (31) and the femur (30) and helps protect the joint. In particular, the meniscus (35) allows the bones (30, 31) to slide freely on each other. A little fluid sac, known as bursa (36) helps the muscles and tendons (e.g., the patellar tendon (32)) slide freely as the knee moves. FIG. 2B also shows that fat tissue (34) is also located within the joint (21).

Osteoarthritis in the knee joint (21) may cause the knee (21) to be stiff, swollen, and painful—thus making it hard to walk, climb, and get in and out of chairs and bathtubs. If not treated, osteoarthritis in the knees (21) can lead to permanent disability.

Figure 3A:
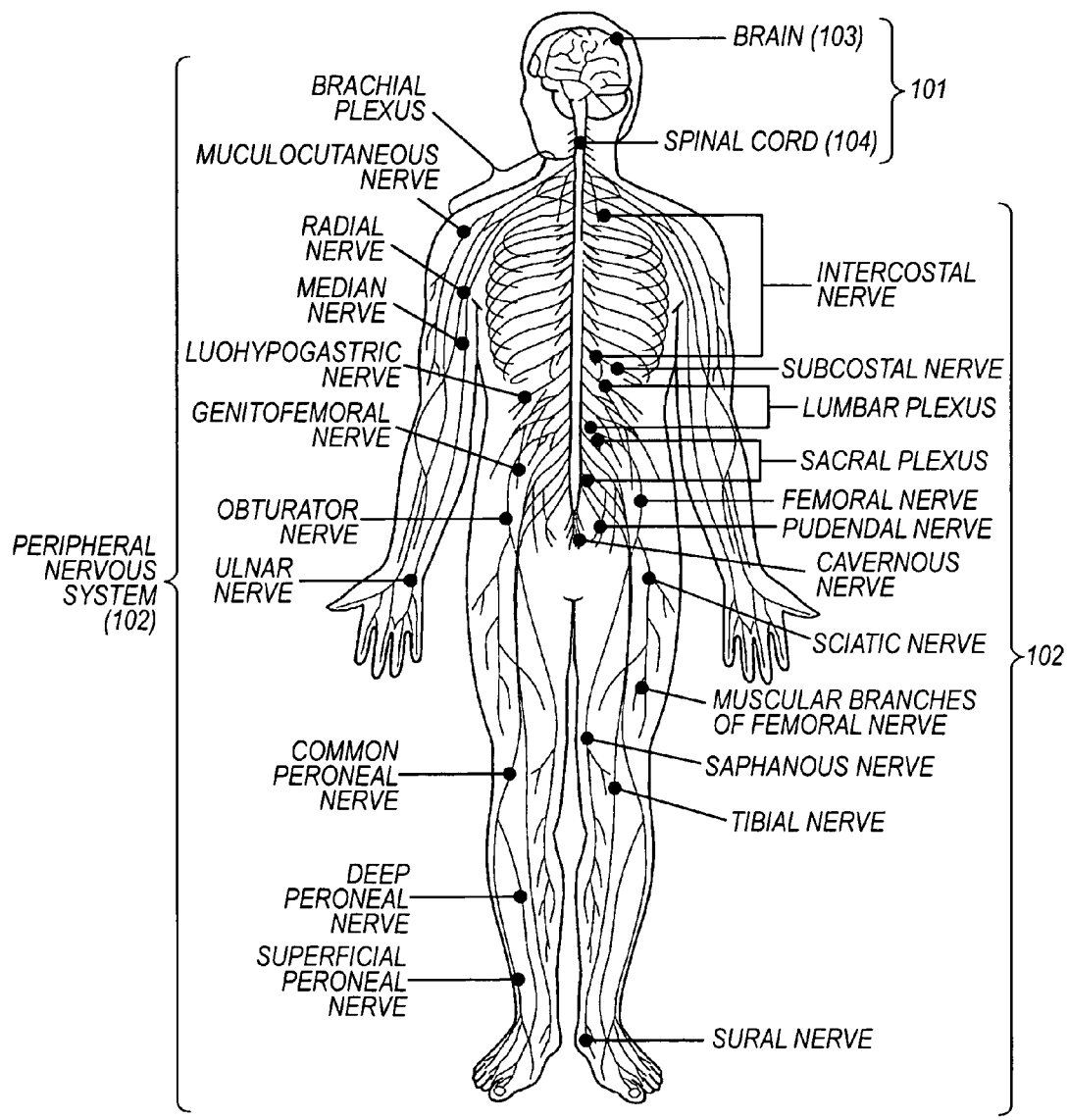
FIG. 3A is a diagram of the human nervous system.

The present specification will describe the use of an implanted SCU to treat these and other conditions connected with osteoarthritis. Before discussing the present methods and systems of treating osteoarthritis, however, a brief overview of the human nervous system will be given. FIG. 3A is a diagram of the human nervous system. The nervous system is divided into a central nervous system (101) and a peripheral nervous system (102). The central nervous system (101) includes the brain (103) and the spinal cord (104). The peripheral nervous system (102) includes a number of nerves that branch from various regions of the spinal cord (104). For example, the peripheral nervous system (102) includes, but is not limited to, the brachial plexus, the musculocutaneous nerve, the radial nerve, the median nerve, the lliohypogastric nerve, the genitorfemoral nerve, the obturator nerve, the ulnar nerve, the peroneal nerve, the sural nerve, the tibial nerve, the saphenous nerve, the femoral nerve, the sciatic nerve, the cavernous nerve, the pudendal nerve, the sacral plexus, the lumbar plexus, the subcostal nerve, and the intercostal nerves.

The peripheral nervous system (102) may be further divided into the somatic nervous system and the autonomic nervous system. The somatic nervous system is the part of the peripheral nervous system (102) associated with the voluntary control of body movements through the action of skeletal muscles. The somatic nervous system consists of afferent fibers which receive information from external sources, and efferent fibers which are responsible for muscle contraction.

Figure 3B:
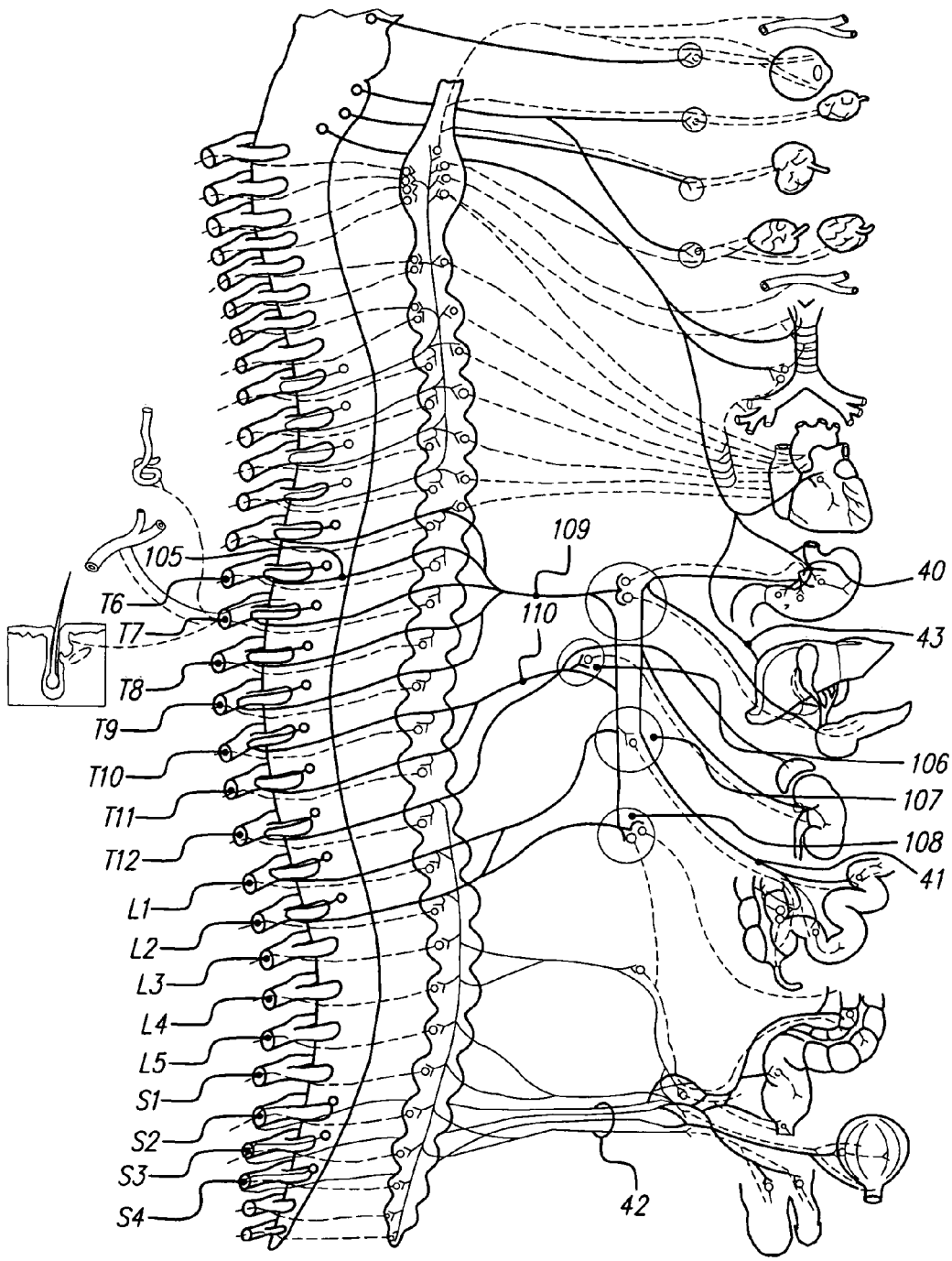
FIG. 3B is a diagram of the autonomic nervous system.

The autonomic nervous system, on the other hand, regulates involuntary action of various organs and is divided into the sympathetic nervous system and the parasympathetic nervous system. FIG. 3B illustrates the autonomic nervous system. FIG. 3B shows the following structures of the parasympathetic nervous system: the anterior or posterior vagus nerves (100), the hepatic branch (101) of the vagus nerve, the celiac branch (102) of the vagus nerve, the gastric branch (103) of the vagus nerve, and branches of the pelvic plexus (104). FIG. 3B also shows the following structures of the sympathetic nervous system: the sympathetic afferent fibers (105) that exit the spinal cord at spinal levels T6, T7, T8, and T9, the sympathetic ganglia (e.g., the celiac (106) ganglia and its subsidiary plexuses, the superior mesenteric ganglia (107), and the inferior mesenteric ganglia (108), the greater splanchnic nerve (109) and the lesser splanchnic nerve (110).

Figure 3C:
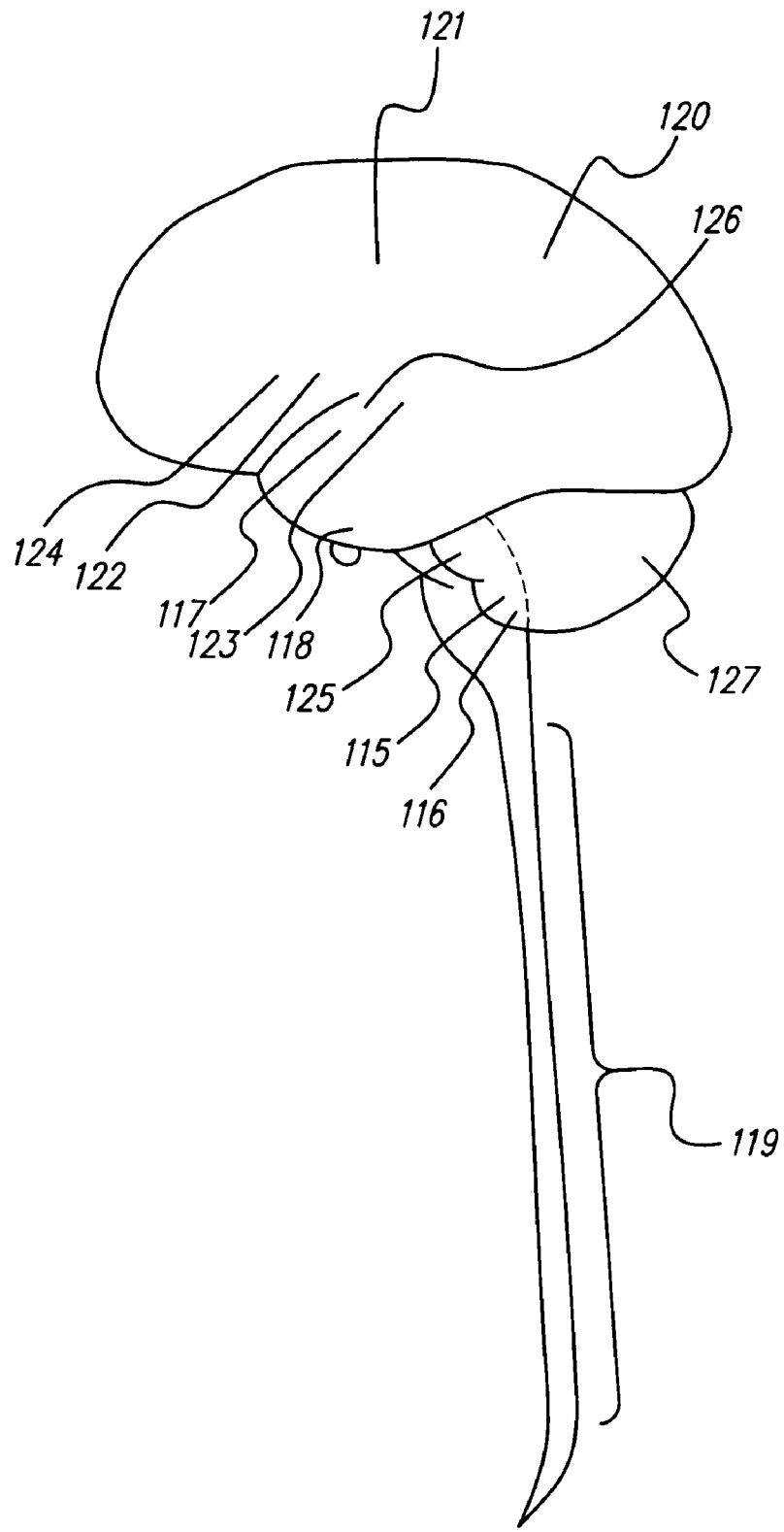
FIG. 3C is a generalized illustration of the central nervous system.

FIG. 3C is a generalized illustration of the central nervous system (101). The central nervous system (101) includes the brain (103) and the spinal cord (104). FIG. 3C shows the approximate locations of the following structures within the brain (103): the cerebellum (127), the nucleus of the solitary tract (115) (located beneath the cerebellum (127)), the dorsal vagal complex (116) (located beneath the cerebellum (127)), the central nucleus of the amygdala (117), the hypothalamus (118) (including the lateral and ventromedial portions of the hypothalamus (118)), the somatosensory cortex (120), the abdominal area of the motor cortex (121), and the pleasure centers in the brain (including the septum pellucidum (122), the ventral striatum (123), the nucleus accumbens (124), the ventral tegmental area (125), and the limbic system (126). In addition, a number of cranial nerves are located at least partially within the brain (103). These cranial nerves may include, but are not limited to, the olfactory, optic, oculomotor, trochlear, trigeminal, abducens, facial, vestibulocochlear, glossopharyngeal, vagus, accessory, and hypoglossal nerves.

Figure 3D:
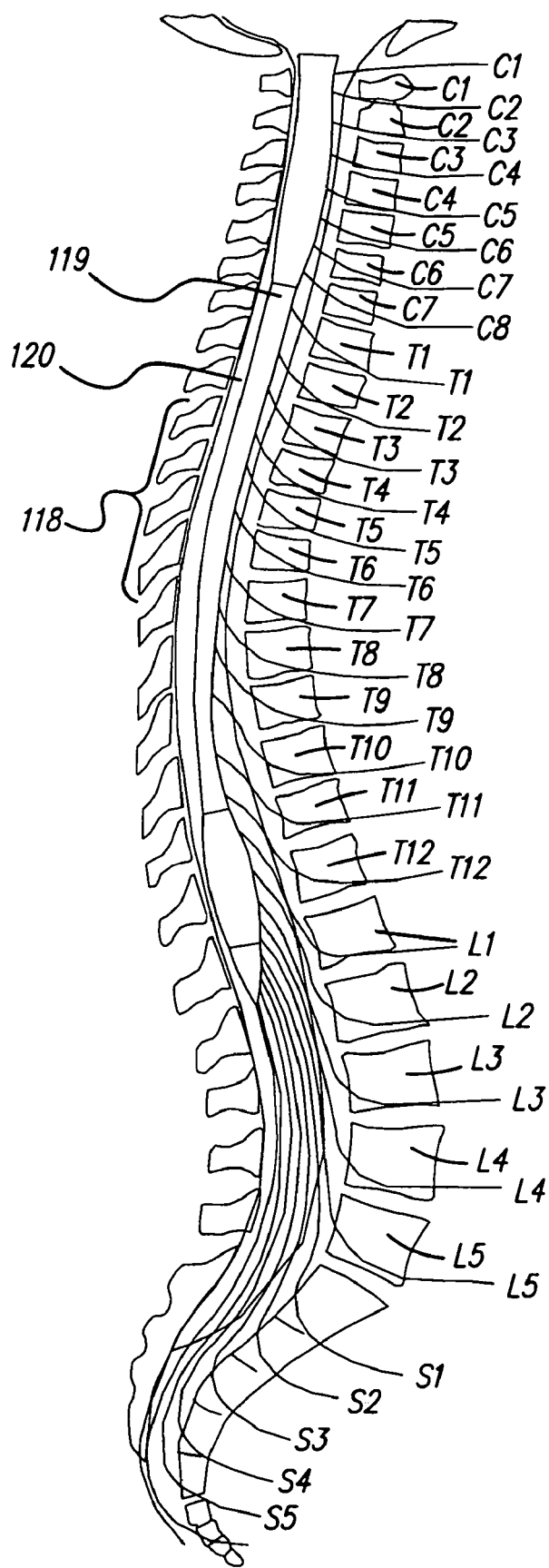
FIG. 3D is a more detailed illustration of the spinal cord of FIG. 3C.

FIG. 3D is a more detailed illustration of the spinal cord (104). As shown in FIG. 3D, the spinal cord (104) is divided into four sections: the cervical region (C1-C8), the thoracic region (T1-T12), the lumbar region (L1-L5), and the sacral region (S1-S5). As mentioned, peripheral nerves branching from the spinal cord (104) innervate different regions of the body. For example, nerves originating in C1-C3 innervate the neck region, nerves originating in C7-C8 innervate the finger region, nerves originating in Ti innervate the hand region, nerves originating in L2 innervate the hip region, and nerves originating in L4-L5 innervate the knee region.

In some embodiments, at least one stimulus is applied with a system control unit (SCU) to one or more stimulation sites within a patient to treat and/or prevent osteoarthritis and/or the symptoms and pathological consequences of osteoarthritis. The terms "stimulus" and "stimulation" will be used interchangeably herein and in the appended claims, unless otherwise specifically denoted, to refer to electrical stimulation, drug stimulation, chemical stimulation, thermal stimulation, electromagnetic stimulation, optical stimulation mechanical stimulation, and/or any other suitable stimulation.

Furthermore, as used herein and in the appended claims, the term "stimulation site" will be used to refer to a location within a patient to which stimulation may be applied to treat osteoarthritis including, but not limited to, one or more of the following: a joint affected by osteoarthritis; an intraarticular joint space of the affected joint; an artery supplying the affected joint; one or more peripheral nerves that innervate the affected joint (e.g., the tibial nerve root or articular branches of the tibial nerve supplying the knee); the spinal cord (e.g., dorsal columns of the spinal cord); spinal segments supplying somatic sensation at the affected joint; spinal segments supplying sympathetic control of the affected joint; the sympathetic ganglia; the nucleus gracilis; the nucleus cuneatis; one or more cranial nerves including, but not limited to, the olfactory, optic, oculomotor, trochlear, trigeminal, abducens, facial, vestibulocochlear, glossopharyngeal, vagus, accessory, and hypoglossal nerves; and/or one or more areas in the brain including, but not limited to, the hypothalamus, thalamus, and the motor cortex. The thalamus and motor cortex are common destinations in the brain for pain signals. Additional or alternative stimulation sites are described in U.S. Pat. No. 6,735,474, U.S. application Ser. No. 09/929,597 ("Fully Implantable Microstimulator for Spinal Nerve, Spinal Nerve Root, and/or Spinal Cord Stimulation as a Therapy for Chronic Pain" to Whitehurst et al.), and U.S. application Ser. No. 11/067,111 ("Methods and Systems for Stimulating a Peripheral Nerve to Treat Chronic Pain" to Whitehurst et al.). These documents are all incorporated herein by reference in their respective entireties.

Many of the above listed stimulation sites are relatively easily accessed. An SCU may thus be implanted via injection and/or via endoscopic means adjacent to one or more of these stimulation sites. In some instances, however, a more complicated surgical procedure may be required for sufficient access to one or more of these stimulation sites and/or for purposes of fixing the SCU in place.

Stimulation of the above listed stimulation sites may treat osteoarthritis via a number of different mechanisms. Four exemplary mechanisms of treating osteoarthritis will be described below. However, it will be recognized that stimulation of any of the above listed stimulation sites may treat osteoarthritis via a mechanism that is different than those described below.

First, electrical stimulation of many of the stimulation sites may block the perception of pain associated with osteoarthritis. There are a number of theories regarding how electrical stimulation inhibit or relieve pain. The most common theory—gate theory or gate control theory—states that stimulation of fast conducting nerves that travel to the spinal cord produces signals that "beat" slower pain-carrying nerve signals and, therefore, override/prevent the message of pain from reaching the spinal cord. Thus, the stimulation closes the "gate" of entry of the pain signals to the spinal cord. Hence, electrical stimulation of a joint affected by osteoarthritis, an intraarticular joint space of the affected joint, one or more peripheral nerves that innervate the affected joint, the spinal cord, spinal segments supplying somatic sensation at the affected joint, spinal segments supplying sympathetic control of the affected joint, the nucleus gracilis, one or more cranial nerves, one or more areas in the brain, the hypothalamus, the thalamus, the motor cortex, and/or any other stimulation site may effectively inhibit or relieve pain associated with osteoarthritis.

Another exemplary mechanism of treating osteoarthritis includes the infusion of drugs, chemicals, and/or other substances designed to or known empirically to treat osteoarthritis. Infusing these drugs, chemicals, and/or other substances directly into the local area of an affected joint or into nerves and/or arteries supplying the joint allows relatively high therapeutic doses while minimizing systemic side effects. These side effects may include, but are not limited to, cardiovascular side effects with COX-2 inhibitors and gastrointestinal side effects with NSAIDs. Hence, the infusion of drugs, chemicals, and/or other substances into a joint affected by osteoarthritis, an intraarticular joint space of the affected joint, an artery supplying the affected joint, one or more peripheral nerves that innervate the affected joint, the spinal cord, spinal segments supplying somatic sensation at the affected joint, spinal segments supplying sympathetic control of the affected joint, the sympathetic ganglia, the nucleus gracilis, one or more cranial nerves, one or more areas in the brain, the hypothalamus, the thalamus, the motor cortex, and/or any other stimulation site may effectively treat with osteoarthritis.

Another exemplary mechanism of treating osteoarthritis includes the stimulation of proprioceptive pathways supplying a joint with osteoarthritis. Patients with poor proprioception (awareness of joint position) often suffer from osteoarthritis. For example, patients with Charcot-Marie-Tooth disorder (CMT), an inherited neurological disease characterized by a slowly progressive degeneration of the muscles in the extremities, often suffer from poor proprioception and from severe osteoarthritis. Stimulation of proprioceptive pathways supplying a joint may, for example, improve patient proprioception through the phenomenon of stochastic resonance. Hence, stimulation of a joint affected by osteoarthritis, an intraarticular joint space of the affected joint, one or more peripheral nerves that innervate the affected joint, the spinal cord, spinal segments supplying sympathetic control of the affected joint, the nucleus gracilis, one or more cranial nerves, one or more areas in the brain, the hypothalamus, the thalamus, the motor cortex, and/or any other stimulation site may effectively treat osteoarthritis by improving patient proprioception.

Another exemplary mechanism of treating osteoarthritis includes modulating the blood supply to a joint affected by osteoarthritis. In some examples, the spinal cord and/or nerves supplying an affected joint may be stimulated to inhibit sympathetic drive responsible for generating vasoconstriction and limiting blood flow to the joint. Alternatively, direct stimulation of the arteries supplying an affected joint may result in dilation of the artery and improved blood flow. Hence, stimulation of an artery supplying the affected joint, one or more peripheral nerves that innervate the affected joint, the spinal cord, spinal segments supplying somatic sensation at the affected joint, spinal segments supplying sympathetic control of the affected joint, the sympathetic ganglia, the nucleus gracilis, one or more cranial nerves, and/or any other stimulation site may effectively treat osteoarthritis by improving the blood supply to the affected joint. Alternatively, the blood flow into a joint affected by osteoarthritis may be decreased by exciting sympathetic drive responsible for generating vasoconstriction. Decreasing the blood flow into a joint may treat osteoarthritis by reducing swelling in the affected joint.

As mentioned, the stimulus applied to the stimulation site may include electrical stimulation, also known as neuromodulation. Electrical stimulation will be described in more detail below. The stimulus may additionally or alternatively include drug stimulation, also referred to herein as drug infusion. As will be described in more detail below, therapeutic dosages of one or more drugs may be infused into a stimulation site or into a site near the stimulation site to treat osteoarthritis. Additionally or alternatively, the stimulus applied to the stimulation site may include any other suitable stimulus such as, but not limited to, chemical stimulation, thermal stimulation, electromagnetic stimulation, optical stimulation, and/or mechanical stimulation.

Figure 4:
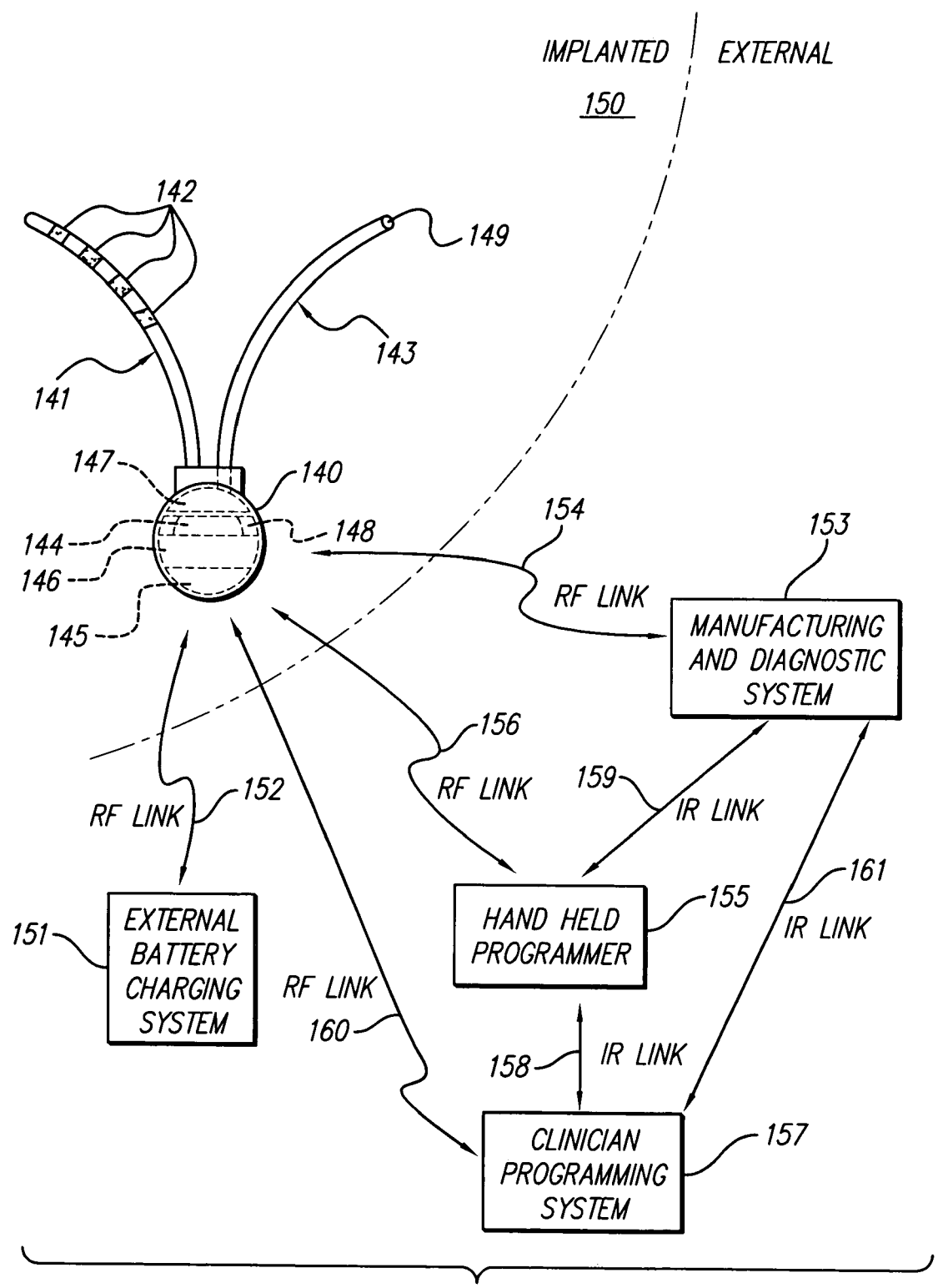
FIG. 4 illustrates an exemplary system control unit (SCU) that may be used to apply stimulation to a stimulation site to treat osteoarthritis according to principles described herein.

In some embodiments, the stimulus may be applied to a stimulation site by using one or more implantable system control units (SCUs). FIG. 4 illustrates an exemplary SCU (140) that may be implanted within a patient (150) and used to apply a stimulus to a stimulation site to treat osteoarthritis, e.g., an electrical stimulation of the stimulation site, an infusion of one or more drugs into the stimulation site, or both. The electrical stimulation function of the SCU (140) will be described first, followed by an explanation of the drug delivery function of the SCU (140). It will be understood, however, that the SCU (140) may be configured to provide any type of stimulation as best suits a particular patient with osteoarthritis.

The exemplary SCU (140) shown in FIG. 4 is configured to provide electrical stimulation to a patient with osteoarthritis and includes a lead (141) having a proximal end coupled to the body of the SCU (140). The lead (141) also includes a number of electrodes (142) configured to apply an electrical stimulation current to a stimulation site. However, the lead (141) may include any number of electrodes (142) as best serves a particular application. The electrodes (142) may be arranged as an array, for example, having at least two or at least four collinear electrodes. In some embodiments, the electrodes are alternatively inductively coupled to the SCU (140). The lead (141) may be thin (e.g., less than 3 millimeters in diameter) such that the lead (141) may be positioned near a stimulation site. Alternatively, as will be described in more detail below, the SCU (140) may be leadless.

As illustrated in FIG. 4, the SCU (140) includes a number of components. It will be recognized that the SCU (140) may include additional and/or alternative components as best serves a particular application. A power source (145) is configured to output voltage used to supply the various components within the SCU (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the SCU (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their entireties. Other battery construction techniques that may be used to make a power source (145) include those shown, e.g., in U.S. Pat. Nos. 6,280,873; 6,458,171, and U.S. Application Publication Nos. 2001/0046625 A1 and 2001/0053476 A1, all of which are incorporated herein by reference in their respective entireties. Recharging can be performed using an external charger.

The SCU (140) may also include a coil (148) configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power from the external device that is used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the SCU (140) via one or more links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs by the SCU (140) into a stimulation site to treat osteoarthritis.

Additionally, if multiple external devices are used in the treatment of a patient, there may be some communication among those external devices, as well as with the implanted SCU (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the SCU (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the SCU (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, glove, sleeve, shirt, knee brace, or the like so as to be positioned near the implanted SCU (140) when in use.

The SCU (140) may also include electrical circuitry (144) configured to produce electrical stimulation pulses that are delivered to the stimulation site via the electrodes (142). In some embodiments, the SCU (140) may be configured to produce monopolar stimulation. The SCU (140) may alternatively or additionally be configured to produce bipolar or tripolar stimulation. Monopolar electrical stimulation is achieved, for example, using the stimulator case as an indifferent electrode. Bipolar or tripolar electrical stimulation is achieved, for example, using one or more of the electrodes of the electrode array as an indifferent electrode. The electrical circuitry (144) may include one or more processors configured to decode stimulation parameters and generate the stimulation pulses. In some embodiments, the SCU (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The SCU (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the SCU (140) to adjust the stimulation parameters such that the stimulation applied by the SCU (140) is safe and efficacious for treatment of a particular patient with osteoarthritis. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused into the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on neural or other tissue. Thus, in some embodiments, the stimulation parameters may be adjusted by the patient, a clinician, or other user of the SCU (140) as best serves a particular stimulation site. The stimulation parameters may also be automatically adjusted by the SCU (140), as will be described below. For example, the amplitude of the stimulation current applied to a stimulation site may be adjusted to have a relatively low value to target a nerve having relatively large diameter fibers. The SCU (140) may also, or alternatively, increase excitement of a stimulation site by applying a stimulation current having a relatively low frequency to the stimulation site (e.g., less than 100 Hz). The SCU (140) may also or alternatively decrease excitement of a stimulation site by applying a relatively high frequency to the stimulation site (e.g., greater than 100 Hz). The SCU (140) may also, or alternatively, be programmed to apply the stimulation current to a stimulation site intermittently or continuously.

In some embodiments, a low amplitude stimulation current is applied to the stimulation site with noise-like frequencies (e.g., random, continually varying, or cyclic frequencies). Low amplitude noise-like stimulation current may enhance proprioception (i.e., the sense of the position of parts of the body, relative to other neighboring parts of the body) through a phenomenon called "stochastic resonance" and allow the patient to have improved control of the alignment of the affected joint.

In some alternative embodiments, the SCU (140) may be configured to apply a high frequency stimulation current to inhibit pain signals on c-fibers or a low frequency stimulation current to inhibit larger diameter afferent axons. Inhibitory stimulation of pain fibers has the effect of reducing the perception of pain caused by osteoarthritis.

Additionally, the exemplary SCU (140) shown in FIG. 4 is configured to provide drug stimulation to a patient with osteoarthritis by applying one or more drugs to a stimulation site. For this purpose, the SCU (140) includes a pump (147). The pump (147) is configured to store and dispense the one or more drugs, for example, through a catheter (143). The catheter (143) is coupled at a proximal end to the SCU (140) and may have an infusion outlet (149) for infusing the one or more drugs into a stimulation site. In some embodiments, the SCU (140) may include multiple catheters (143) and/or pumps (147) for storing and infusing dosages of the one or more drugs into the stimulation site or into multiple stimulation sites.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The one or more drugs that may be applied to a stimulation site to treat osteoarthritis may have an excitatory effect on the stimulation site. Additionally or alternatively, the one or more drugs may have an inhibitory effect on the stimulation site to treat osteoarthritis. Exemplary excitatory drugs that may be applied to a stimulation site to treat osteoarthritis include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat osteoarthritis include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat osteoarthritis include at least one or more of the following substances: analgesics, opioids (e.g., codeine, oxycodone, propoxyphene), acetaminophen, non-steroidal anti-inflammatory medications (NSAIDS) (e.g., ibuprofen, naproxen, COX-2 inhibitors); corticosteroids (e.g., triamcinolone, hexacetonide, solumedrol), hyaluronic acid derivatives (e.g., hylan G-F 20), colchicines, and hydroxychloroquine.

Any of the drugs listed above, alone or in combination, or other drugs or combinations of drugs developed or shown to treat osteoarthritis or its symptoms may be applied to the stimulation site to treat osteoarthritis. In some embodiments, the one or more drugs are infused chronically into the stimulation site. Additionally or alternatively, the one or more drugs may be infused acutely into the stimulation site in response to a biological signal or a sensed need for the one or more drugs.

The SCU (140) of FIG. 4 is illustrative of many types of SCUs that may be used to treat osteoarthritis. For example, the SCU (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus to a stimulation site within a patient. Exemplary IPGs suitable for use as described herein include, but are not necessarily limited to, those disclosed in U.S. Pat. Nos. 6,381,496, 6,553,263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938,688; 6,016,449; and 6,539,263. All of these listed patents are incorporated herein by reference in their respective entireties.

Alternatively, the SCU (140) may be or include an implantable microstimulator, such as a BION® microstimulator (Advanced Bionics® Corporation, Valencia, Calif.). Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 5:
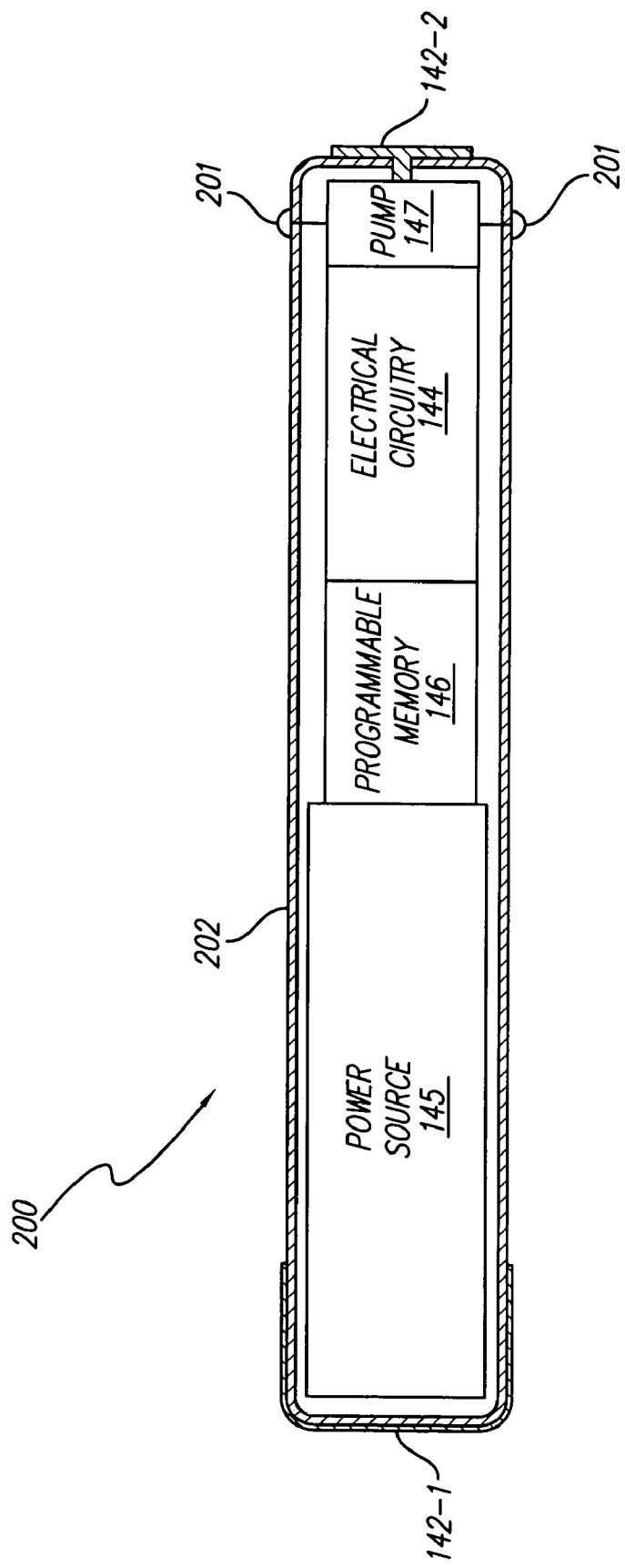
FIG. 5 illustrates an exemplary microstimulator that may be used as an SCU to apply stimulation to a stimulation site to treat osteoarthritis according to principles described herein.

FIG. 5 illustrates an exemplary BION microstimulator (200) that may be used as the SCU (140; FIG. 4) described herein. Other configurations of the microstimulator (200) are possible, as shown in the above-referenced patents and as described further below.

As shown in FIG. 5, the microstimulator (200) may include the power source (145), the programmable memory (146), the electrical circuitry (144), and the pump (147) described in connection with FIG. 4. These components are housed within a capsule (202). The capsule (202) may be a thin, elongated cylinder or any other shape as best serves a particular application. The shape of the capsule (202) may be determined by the structure of the desired stimulation site, the surrounding area, and/or the method of implantation. In some embodiments, the capsule (202) has a volume that is substantially equal to or less than three cubic centimeters.

In some embodiments, the microstimulator (200) may include two or more leadless electrodes (142). Either or both of the electrodes (142) may alternatively be located at the ends of short, flexible leads as described in U.S. Application Publication No. 2003/0114905 A1, which is incorporated herein by reference in its entirety. The use of such leads permits, among other things, electrical stimulation current to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, polymers, metal, or any other material that provides a hermetic package that will exclude water vapor but permit the passage of electromagnetic fields used to transmit data and/or power. The electrodes (142) may be made of a conducting ceramic, conducting polymer, and/or a noble or refractory metal, such as gold, silver, platinum, iridium, tantalum, titanium, titanium nitride, niobium or their alloys that are biocompatible, e.g., minimize corrosion, electrolysis, and damage to the surrounding tissues.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques. The microstimulator (200) may also be implanted and, in some cases, fixed in place, through an incision. As previously mentioned, the microstimulator (200) may be coupled directly to a stimulation site.

FIG. 5 shows that the microstimulator (200) may also include one or more infusion outlets (201). The infusion outlets (201) facilitate the infusion of one or more drugs into a stimulation site to treat a particular medical condition. The infusion outlets (201) may dispense one or more drugs, chemicals, or other substances directly to the stimulation site. Alternatively, as will be described in more detail below, catheters may be coupled to the infusion outlets (201) to deliver the drug therapy to a stimulation site some distance from the body of the microstimulator (200). The stimulator (200) of FIG. 5 also includes electrodes (142-1 and 142-2) at either end of the capsule (202). One of the electrodes (142) may be designated as a stimulating electrode to be placed close to the stimulation site and one of the electrodes (142) may be designated as an indifferent electrode used to complete a stimulation circuit.

Figure 6:
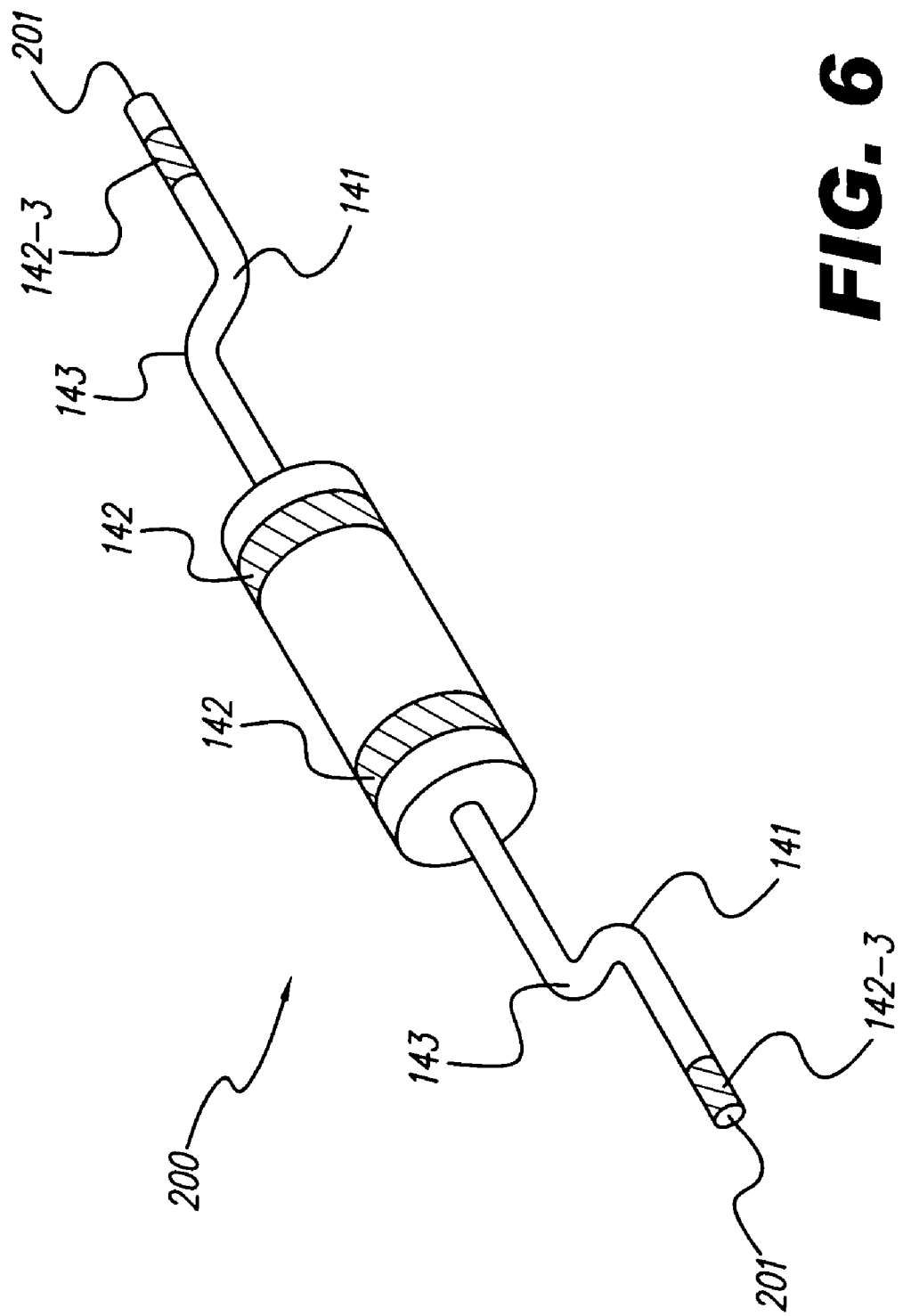
FIG. 6 shows one or more catheters coupled to the microstimulator according to principles described herein.

FIG. 6 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 6, a drug therapy is expelled by the pump (147, FIG. 5) from an infusion outlet (201, FIG. 5) in the casing (202, FIG. 5) of the microstimulator (200), through the catheter (143), out an infusion outlet (201) at the end of the catheter (143) to the stimulation site within the patient. As shown in FIG. 6, the catheters (143) may also serve as leads (141) having one or more electrodes (142-3) disposed thereon. Thus, the catheters (143) and leads (141) of FIG. 6 permit infused drugs and/or electrical stimulation current to be directed to a stimulation site while allowing most elements of the microstimulator (200) to be located in a more surgically convenient site. The example of FIG. 6 may also include leadless electrodes (142) disposed on the housing of the microstimulator (200), in the same manner described above.

Figure 7:
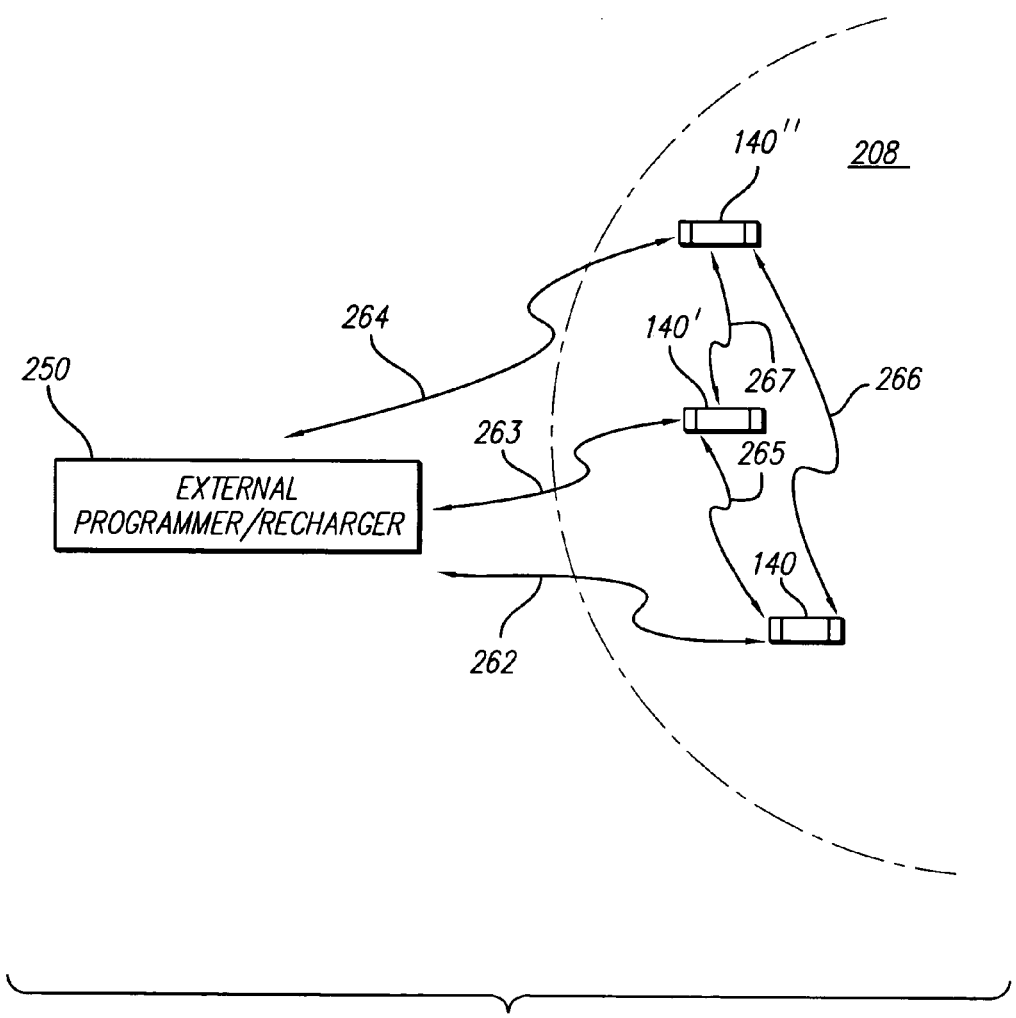
FIG. 7 depicts a number of SCUs configured to communicate with each other and/or with one or more external devices according to principles described herein.

Returning to FIG. 4, the SCU (140) may be configured to operate independently. Alternatively, as shown in FIG. 7 and described in more detail below, the SCU (140) may be configured to operate in a coordinated manner with one or more additional SCUs, other implanted devices, or other devices external to the patient's body. For instance, a first SCU may control or operate under the control of a second SCU, other implanted device, or other device external to the patient's body. The SCU (140) may be configured to communicate with other implanted SCUs, other implanted devices, or other devices external to the patient's body via an RF link, an ultrasonic link, an optical link, or any other type of communication link. For example, the SCU (140) may be configured to communicate with an external remote control unit that is capable of sending commands and/or data to the SCU (140) and that is configured to receive commands and/or data from the SCU (140).

In order to determine the amount and/or type(s) of stimulating drug(s) and/or the strength and/or duration of electrical stimulation required to most effectively treat osteoarthritis, various indicators of osteoarthritis and/or a patient's response to treatment may be sensed or measured. These indicators include, but are not limited to, synovial fluid levels within an affected joint; mechanical properties of the synovial fluid (e.g., viscosity); distance across an affected joint; pressure distribution across an affected joint or pressure magnitude experienced by the affected joint; mechanical properties of joint motion (e.g., vibration, range of motion, activity level, smoothness of trajectory); forces exerted by muscles surrounding an affected joint; electrical activity of the brain (e.g., EEG); neurotransmitter levels; hormone levels; metabolic activity in the brain; blood flow rate in the affected joint and/or one or more tissues within the body; temperature in superficial tissues; and/or medication levels within the patient. In some embodiments, the SCU (140) may be configured to change the stimulation parameters in a closed loop manner in response to these measurements. The SCU (140) may be configured to perform the measurements. Alternatively, other sensing devices may be configured to perform the measurements and transmit the measured values to the SCU (140). Exemplary sensing devices include, but are not limited to, chemical sensors, electrodes, optical sensors, mechanical (e.g., motion, pressure) sensors, and temperature sensors.

Thus, one or more external appliances may be provided to interact with the SCU (140), and may be used to accomplish at least one or more of the following functions:

Function 1: If necessary, transmit electrical power to the SCU (140) in order to power the SCU (140) and/or recharge the power source (145).

Function 2: Transmit data to the SCU (140) in order to change the stimulation parameters used by the SCU (140).

Function 3: Receive data indicating the state of the SCU (140) (e.g., battery level, drug level, stimulation parameters, etc.).

Additional functions may include adjusting the stimulation parameters based on information sensed by the SCU (140) or by other sensing devices.

By way of example, an exemplary method of treating a patient with osteoarthritis may be carried out according to the following sequence of procedures. The steps listed below may be modified, reordered, and/or added to as best serves a particular application.

1. An SCU (140) is implanted so that its electrodes (142) and/or infusion outlet (149) are coupled to or located near a stimulation site (e.g., the affected joint). If the SCU (140) is a microstimulator, such as the BION microstimulator (200; FIG. 5), the microstimulator itself may be coupled to the stimulation site.

2. The SCU (140) is programmed to apply at least one stimulus to the stimulation site. The stimulus may include electrical stimulation, drug stimulation, chemical stimulation, thermal stimulation, electromagnetic stimulation, optical stimulation, mechanical stimulation, and/or any other suitable stimulation.

3. When the patient desires to invoke stimulation, the patient sends a command to the SCU (140) (e.g., via a remote control) such that the SCU (140) delivers the prescribed stimulation. The SCU (140) may be alternatively or additionally configured to automatically apply the stimulation in response to sensed indicators of osteoarthritis.

4. To cease stimulation, the patient may turn off the SCU (140) (e.g., via a remote control).

5. Periodically, the power source (145) of the SCU (140) is recharged, if necessary, in accordance with Function 1 described above.

In other examples, the treatment administered by the SCU (140), i.e., drug therapy and/or electrical stimulation, may be automatic and not controlled or invoked by the patient.

For the treatment of different patients with osteoarthritis, it may be desirable to modify or adjust the algorithmic functions performed by the implanted and/or external components, as well as the surgical approaches. For example, in some situations, it may be desirable to employ more than one SCU (140), each of which could be separately controlled by means of a digital address. Multiple channels and/or multiple patterns of stimulation may thereby be used to deal with multiple symptoms of osteoarthritis.

For instance, as shown in the example of FIG. 7, a first SCU (140) implanted beneath the skin of the patient (208) provides a stimulus to a first location; a second SCU (140') provides a stimulus to a second location; and a third SCU (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. SCU (140), may control or operate under the control of another implanted device(s), e.g. SCU (140') and/or SCU (140"). Control lines (262-267) have been drawn in FIG. 7 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple SCUs (140) operating in a coordinated manner, the first and second SCUs (140, 140') of FIG. 7 may be configured to sense various indicators of osteoarthritis and transmit the measured information to the third SCU (140"). The third SCU (140") may then use the measured information to adjust its stimulation parameters and apply stimulation to a stimulation site accordingly. The various implanted SCUs may, in any combination, sense indicators of osteoarthritis, communicate or receive data on such indicators, and adjust stimulation parameters accordingly.

Alternatively, the external device (250) or other external devices communicating with the external device may be configured to sense various indicators of a patient's condition. The sensed indicators can then be collected by the external device (250) for relay to one or more of the implanted SCUs or may be transmitted directly to one or more of the implanted SCUs by any of an array of external sensing devices. In either case, the SCU, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the SCUs to adjust stimulation parameters accordingly.

The SCU (140) of FIG. 4 may be implanted within the patient (150) using any suitable joint arthroscopy tool or surgical procedure such as, but not limited to, injection, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501,703; 6,487,446; and 6,516,227. Exemplary methods of implanting a deep brain stimulator, for example, are described in U.S. Pat. Nos. 5,938,688; 6,016,449; and 6,539,263. All of these listed patents are incorporated herein by reference in their respective entireties.

Figure 8A:
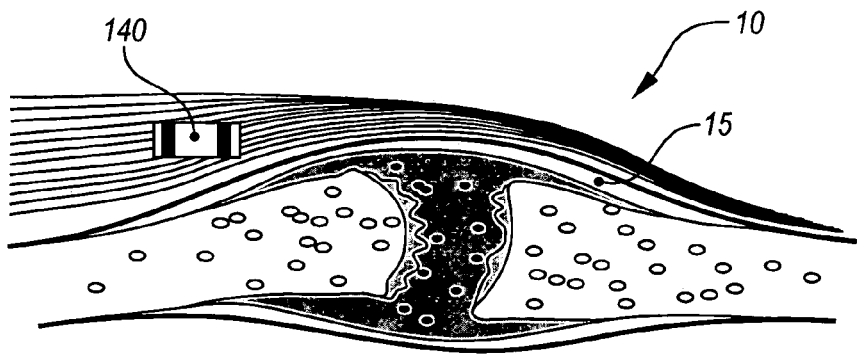
FIG. 8A illustrates an exemplary SCU implanted near a joint affected by osteoarthritis according to principles described herein.

The SCU (140) may be implanted at a number of different implant sites. For example, as shown in FIG. 8A, the SCU (140) may be implanted adjacent to or near an affected joint and configured to stimulate the nerves and/or tissue surrounding the joint. Alternatively, the SCU (140) may be coupled directly to the joint capsule. An SCU (140) coupled to a lead (141) may alternatively be implanted at an implant site relatively far from the affected joint. In this case, the lead (141) maybe routed from the SCU (140) to a location near the affected joint.

Figure 8B:
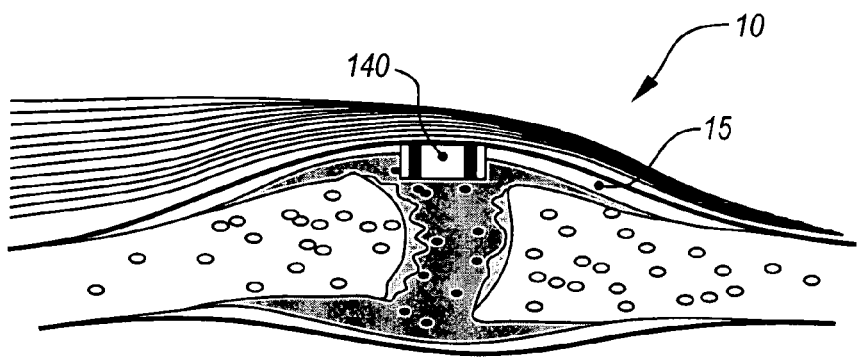
FIG. 8B illustrates an exemplary SCU coupled directly to the synovial membrane of a joint that is affected by osteoarthritis according to principles described herein.

In some embodiments, as shown in FIG. 8B, the SCU (140) may be implanted entirely within an affected joint (e.g., the knee joint (21; FIG. 2B)). The SCU (140) may be implanted within the joint using any suitable joint arthroscopy tool or surgical procedure such as, but not limited to, injection, small incision, open placement, laparoscopy, or endoscopy. For example, the SCU (140) may be sutured directly to the synovial membrane (15), as illustrated in FIG. 8B. In some examples, the joint capsule forms a protective coating around the implanted SCU (140) such that movement of the SCU (140) is minimized.

Figure 8C:
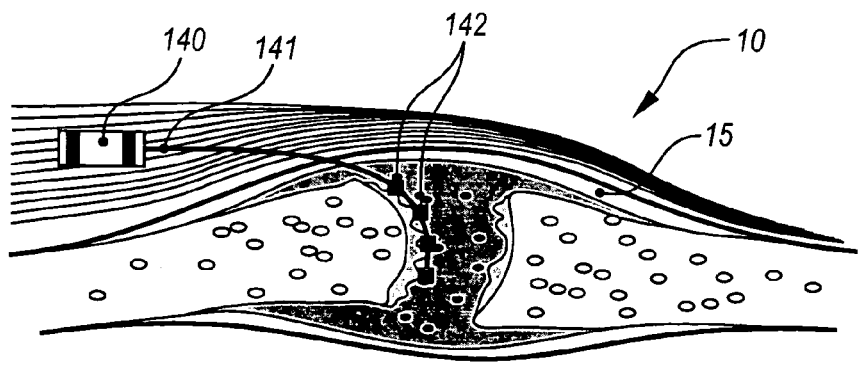
FIG. 8C illustrates an exemplary SCU implanted in tissue near a joint that is affected by osteoarthritis according to principles described herein.

In some alternative embodiments, a lead (141) that is coupled to an SCU (140) is inserted into the affected joint, as illustrated in FIG. 8C. In this case, the SCU (140) is implanted at a location outside the affected joint. The lead (141) may be implanted within the joint using any suitable joint arthroscopy tool or surgical procedure such as, but not limited to, injection, small incision, open placement, laparoscopy, or endoscopy. An antiseptic may be applied to the surface of the joint around the point of entry to prevent infection.

Figure 9:
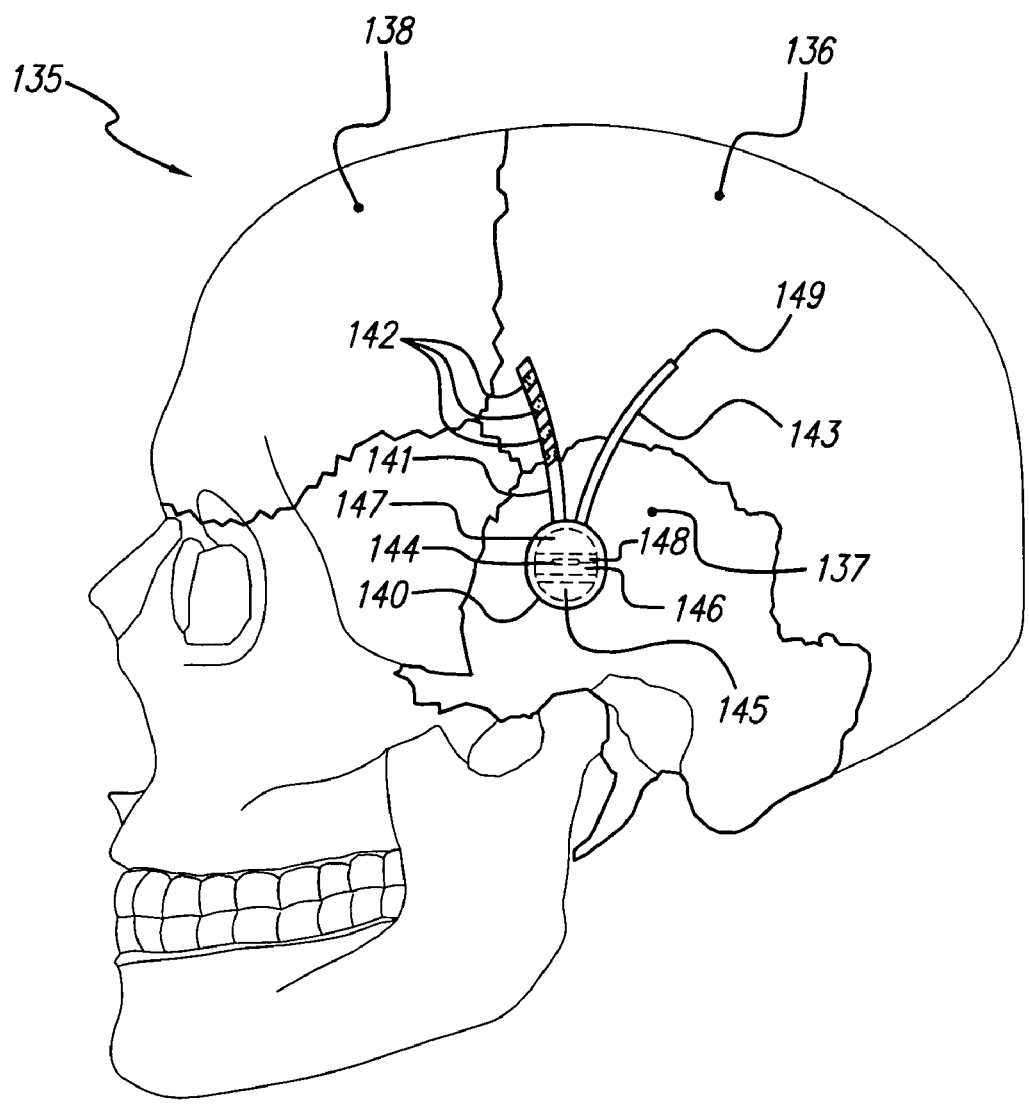
FIG. 9 shows an SCU implanted in the skull according to principles described herein.

By way of further example, FIG. 9 shows an SCU (140) (e.g., a deep brain stimulator) that has been implanted beneath the scalp of a patient to stimulate a nerve associated with pain in the affected joint. The SCU (140) may be implanted in a surgically-created shallow depression or opening in the skull (135). For instance, the depression may be made in the parietal bone (136), temporal bone (137), frontal bone (138), or any other bone within the skull (135) as best serves a particular application. The SCU (140) may conform to the profile of surrounding tissue(s) and/or bone(s), thereby minimizing the pressure applied to the skin or scalp. In some embodiments, the lead (141) and/or catheter (143) run subcutaneously to an opening in the skull (135) and pass through the opening into or onto a stimulation site in the brain, cervical spinal cord, thalamus, cortex, or any other location within the patient.

Figure 10:
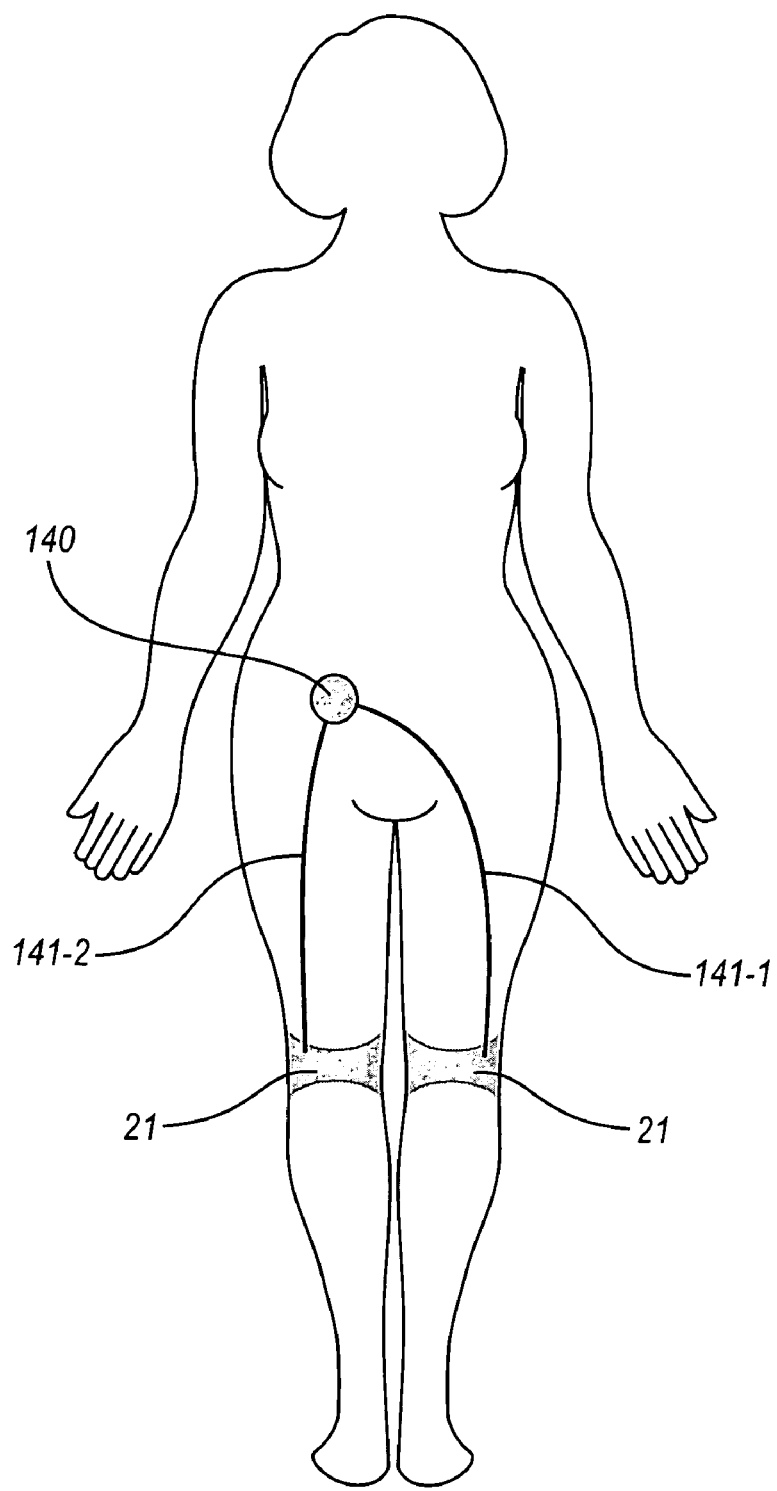
FIG. 10 shows an SCU configured to stimulate the joints in both knees according to principles described herein.

In some examples, the SCU (140) may stimulate multiple stimulation sites. For example, FIG. 10 shows an SCU (140) configured to stimulate the joints in both knees (21). As shown in FIG. 10, the SCU (140) may be implanted in a surgically convenient location, such as the buttocks. A first lead (141-1) is coupled to the SCU (140) and routed to one of the knees (21). A second lead (141-2), also coupled to the SCU (140), is routed to the other knee (21). In this manner, stimulation may be applied to both knee joints (21). Likewise, multiple leads (141) coupled to any number of SCUs (140) may be routed to other affected joints or stimulation sites as best serves a particular application.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with osteoarthritis, said method comprising:
    implanting a system control unit at least partially within said patient;
    configuring one or more stimulation parameters to treat osteoarthritis;
    programming said system control unit with said one or more stimulation parameters;
    generating a stimulus configured to treat said osteoarthritis with said system control unit in accordance with said one or more stimulation parameters; and
    applying said stimulus to a stimulation site within said patient;
    wherein said stimulation site comprises at least one or more of an artery supplying a joint affected by said osteoarthritis, a spinal cord, a spinal segment supplying somatic sensation at said affected joint, a spinal segment supplying sympathetic control of said affected joint, a sympathetic ganglia, a nucleus gracilis, a nucleus cuneatis, a cranial nerve, a deep brain location, a hypothalamus, a thalamus, and a motor cortex;
    wherein said system control unit is coupled to one or more electrodes disposed on an outer surface of said system control unit; and
    wherein said stimulus comprises a stimulation current delivered to said stimulation site via said electrodes.

2. The method of claim 1, further comprising coupling said system control unit to said stimulation site.

3. The method of claim 1, wherein said stimulus further comprises one or more drugs delivered to said stimulation site.

4. The method of claim 1, further comprising sensing at least one indicator related to said osteoarthritis and using said at least one sensed indicator to adjust one or more of said stimulation parameters.

5. The method of claim 4, wherein said at least one indicator comprises at least one or more of a synovial fluid level within said affected joint, the viscosity of synovial fluid within said affected joint, a distance across said affected joint, a pressure distribution across said affected joint, a vibration resulting from movement of said affected joint, a range of motion of said affected joint, an activity level of said affected joint, a smoothness of trajectory of said joint, a force exerted by one or more muscles surrounding said affected joint, electrical brain activity, a neurotransmitter level, a hormone level, a blood flow rate in said affected joint, and a medication level.

6. The method of claim 1, wherein said system control unit comprises a microstimulator.

7. A method of treating a patient with osteoarthritis, said method comprising:
    implanting a system control unit within said patient;
    configuring one or more stimulation parameters to treat osteoarthritis;
    programming said system control unit with said one or more stimulation parameters;
    generating a stimulation current configured to treat said osteoarthritis with said system control unit in accordance with said one or more stimulation parameters; and
    applying said stimulation current to a stimulation site within said patient;
    wherein said stimulation site comprises an artery supplying a joint affected by said osteoarthritis.

8. The method of claim 7, further comprising coupling said system control unit to said stimulation site.

9. The method of claim 7, further comprising sensing at least one indicator related to said osteoarthritis and using said at least one sensed indicator to adjust one or more of said stimulation parameters.

10. The method of claim 9, wherein said at least one indicator comprises at least one or more of a synovial fluid level within said affected joint, the viscosity of synovial fluid within said affected joint, a distance across said affected joint, a pressure distribution across said affected joint, a vibration resulting from movement of said affected joint, a range of motion of said affected joint, an activity level of said affected joint, a smoothness of trajectory of said joint, a force exerted by one or more muscles surrounding said affected joint, electrical brain activity, a neurotransmitter level, a hormone level, a blood flow rate in said affected joint, and a medication level.

11. The method of claim 7, further comprising delivering one or more drugs to said stimulation site.

12. The method of claim 1, wherein the stimulation site comprises the spinal cord.

13. The method of claim 1, wherein the stimulation site comprises the spinal segment supplying somatic sensation at said affected joint.

14. The method of claim 1, wherein the stimulation site comprises the spinal segment supplying sympathetic control of said affected joint.

15. The method of claim 1, wherein the stimulation site comprises the sympathetic ganglia.

16. The method of claim 1, wherein the stimulation site comprises the nucleus gracilis.

17. The method of claim 1, wherein the stimulation site comprises the nucleus cuneatis.

18. The method of claim 1, wherein the stimulation site comprises the cranial nerve.

19. The method of claim 1, wherein the stimulation site comprises the hypothalamus.

20. The method of claim 1, wherein the stimulation site comprises the thalamus.

* * * * *

UNITED STATES PATENT AND TRADEMARK OFFICE
CERTIFICATE OF CORRECTION

PATENT NO. : 7,610,100 B2  
APPLICATION NO. : 11/322763  
DATED : October 27, 2009  
INVENTOR(S) : Jaax et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this

Twelfth Day of October, 2010

David J. Kappos  
*Director of the United States Patent and Trademark Office*